United States Patent
Bonan et al.

(10) Patent No.: US 8,012,078 B2
(45) Date of Patent: Sep. 6, 2011

(54) METHODS AND APPARATUS EMPLOYING IONIZING RADIATION FOR TREATMENT OF CARDIAC ARRHYTHMIA

(75) Inventors: Raoul Bonan, Mirabel (CA); Charles E. Larsen, Cumming, GA (US); Roelof Trip, Lawrenceville, GA (US); Douglas B. Schumer, Atlanta, GA (US); Jack C. Griffis, III, Decatur, GA (US); Andrew L. Lerohl, Hoschton, GA (US)

(73) Assignee: Best Vascular, Norcross, GA (US)

( * ) Notice: Subject to any disclaimer, the term of this patent is extended or adjusted under 35 U.S.C. 154(b) by 1169 days.

(21) Appl. No.: 11/709,652

(22) Filed: Feb. 22, 2007

(65) Prior Publication Data

US 2007/0173812 A1   Jul. 26, 2007

(51) Int. Cl.
*A61N 5/00* (2006.01)
(52) U.S. Cl. .................................................. 600/3
(58) Field of Classification Search ........... 600/1–8; 128/897, 898
See application file for complete search history.

(56) References Cited

U.S. PATENT DOCUMENTS

| | | |
|---|---|---|
| 4,886,067 A | 12/1989 | Palermo |
| 5,263,493 A | 11/1993 | Avitall |
| 5,267,960 A | 12/1993 | Hayman et al. |
| 5,281,213 A | 1/1994 | Milder et al. |
| 5,364,352 A | 11/1994 | Cimino et al. |
| 5,484,384 A | 1/1996 | Fearnot |
| 5,540,659 A | 7/1996 | Teirstein |
| 5,680,860 A | 10/1997 | Imran |
| 5,683,345 A | 11/1997 | Waksman et al. |
| 5,816,999 A * | 10/1998 | Bischoff et al. ............ 600/3 |
| 5,891,136 A | 4/1999 | McGee et al. |
| 5,899,882 A | 5/1999 | Waksman et al. |
| 5,925,038 A | 7/1999 | Panescu et al. |
| 6,013,020 A | 1/2000 | Meloul et al. |
| 6,019,718 A * | 2/2000 | Hektner ............... 600/3 |
| 6,030,360 A | 2/2000 | Biggs |
| 6,050,930 A * | 4/2000 | Teirstein ............. 600/3 |
| 6,052,607 A | 4/2000 | Edwards et al. |
| 6,063,078 A | 5/2000 | Wittkampf |
| 6,120,476 A | 9/2000 | Fung et al. |
| 6,163,716 A | 12/2000 | Edwards et al. |
| 6,179,835 B1 | 1/2001 | Panescu et al. |
| 6,224,536 B1 | 5/2001 | Pike |

(Continued)

FOREIGN PATENT DOCUMENTS

EP    0 605 796 A2    7/1997

(Continued)

OTHER PUBLICATIONS

European Search Report re application No. EP 02768885.2, dated Jul. 22, 2008.

(Continued)

*Primary Examiner* — Samuel Gilbert
(74) *Attorney, Agent, or Firm* — Jason Freeman; Oneal R. Mistry; Best Vascular

(57) ABSTRACT

Method and apparatus are disclosed employing ionizing radiation for forming lines of ablation or lesions in cardiac tissue to treat atrial fibrillation or other electrophysiological problems with the heart. The apparatus may include a catheter in which the radiation source is advanced hydraulically after the catheter is in place within the heart. Various fixation devices are also disclosed for fixing the location of the catheter within the heart.

47 Claims, 8 Drawing Sheets

U.S. PATENT DOCUMENTS

| | | |
|---|---|---|
| 6,254,601 B1 | 7/2001 | Burbank et al. |
| 6,258,019 B1 | 7/2001 | Verin et al. |
| 6,261,219 B1 | 7/2001 | Meloul et al. |
| 6,267,760 B1 | 7/2001 | Swanson |
| 6,306,073 B1 | 10/2001 | Weinberger |
| 6,306,074 B1 | 10/2001 | Waksman et al. |
| 6,333,020 B1 | 12/2001 | Wallace et al. |
| 6,366,808 B1 | 4/2002 | Schroeppel et al. |
| 6,400,980 B1 | 6/2002 | Lemelson |
| 6,413,204 B1 | 7/2002 | Winkler et al. |
| 6,458,070 B1 | 10/2002 | Waksman et al. |
| 6,503,185 B1 | 1/2003 | Waksman et al. |
| 6,514,191 B1 | 2/2003 | Popowski et al. |
| 6,540,655 B1 * | 4/2003 | Chin et al. ............. 600/3 |
| 6,602,251 B2 | 8/2003 | Burbank et al. |
| 6,616,591 B1 | 9/2003 | Teoh et al. |
| 6,955,640 B2 | 10/2005 | Sanders et al. |
| 2001/0009970 A1 | 7/2001 | Chornenky et al. |
| 2001/0012918 A1 | 8/2001 | Swanson |
| 2001/0051766 A1 | 12/2001 | Gazdzinski |
| 2002/0026188 A1 | 2/2002 | Balbierz et al. |
| 2002/0077676 A1 | 6/2002 | Schroeppel et al. |
| 2002/0165529 A1 | 11/2002 | Danek |
| 2003/0028187 A1 | 2/2003 | Vaska et al. |
| 2003/0050637 A1 | 3/2003 | Maguire et al. |
| 2003/0060820 A1 | 3/2003 | Maguire et al. |
| 2003/0078571 A1 | 4/2003 | Sliwa, Jr. et al. |
| 2003/0079753 A1 | 5/2003 | Vaska et al. |
| 2003/0153905 A1 | 8/2003 | Edwards et al. |
| 2003/0159700 A1 | 8/2003 | Laufer et al. |
| 2003/0171746 A1 | 9/2003 | Fleischman |
| 2003/0176758 A1 | 9/2003 | Nakano et al. |
| 2003/0199867 A1 | 10/2003 | Wellman |
| 2003/0208195 A1 | 11/2003 | Thompson et al. |
| 2003/0212394 A1 | 11/2003 | Pearson et al. |
| 2003/0225309 A1 | 12/2003 | Teoh et al. |

FOREIGN PATENT DOCUMENTS

| | | |
|---|---|---|
| EP | 0 904 796 A2 | 3/1999 |
| WO | WO 96/40344 A1 | 12/1996 |
| WO | WO 99/09919 | 3/1999 |
| WO | WO 00/06242 A1 | 2/2000 |

OTHER PUBLICATIONS

International Search Report re application No. PCT/US02/30159, dated Mar. 18, 2003.

International Preliminary Examinatin Report re application No. PCT/US02/30159, dated Sep. 27, 2004.

European Supplementary Partial Search Report dated Aug. 23, 2007 for co-pending EP application No. EP 02768885.2-2305 based on PCT/US0230159.

* cited by examiner

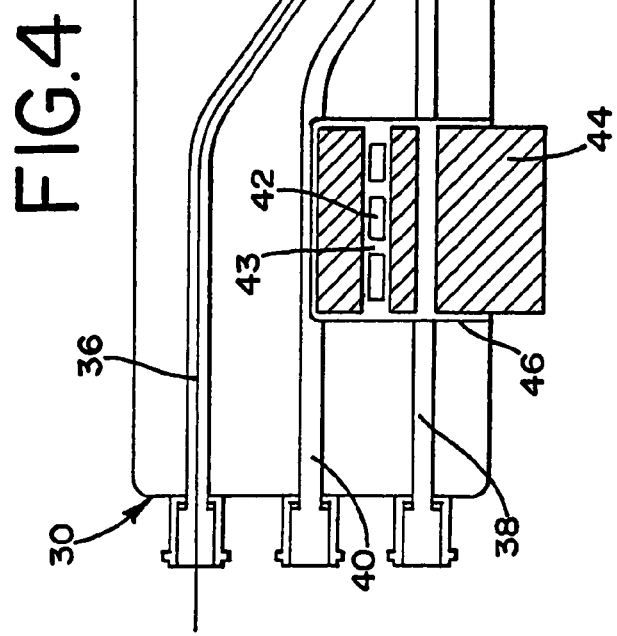
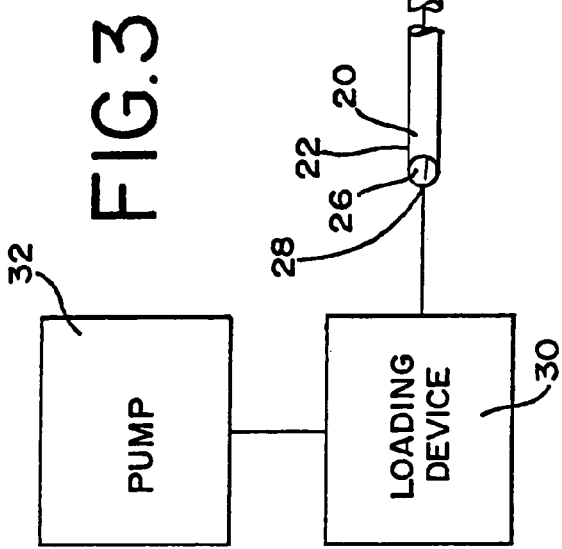
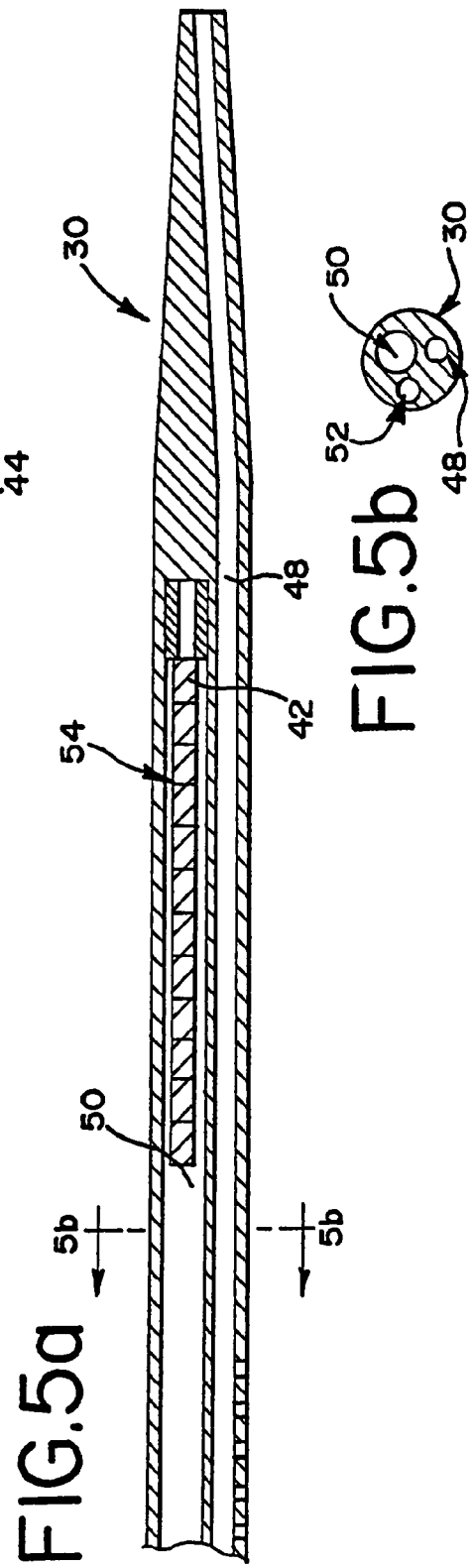

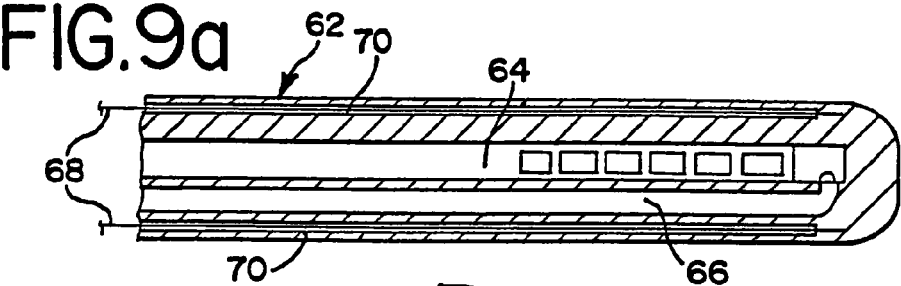
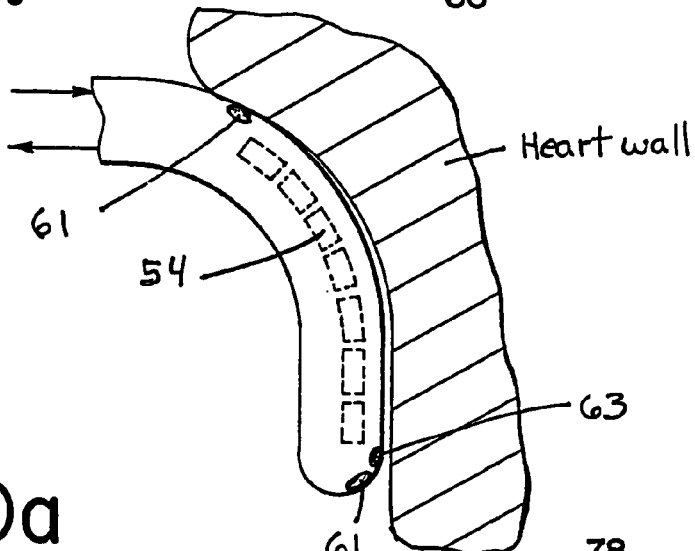
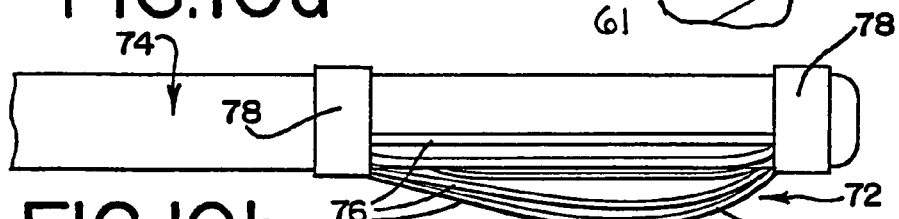
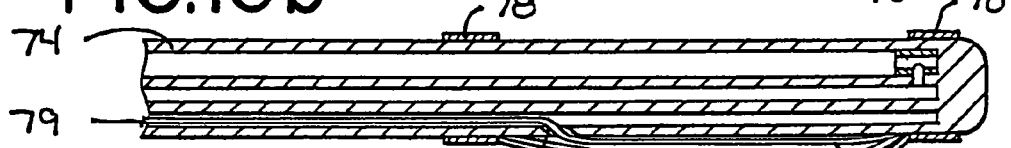
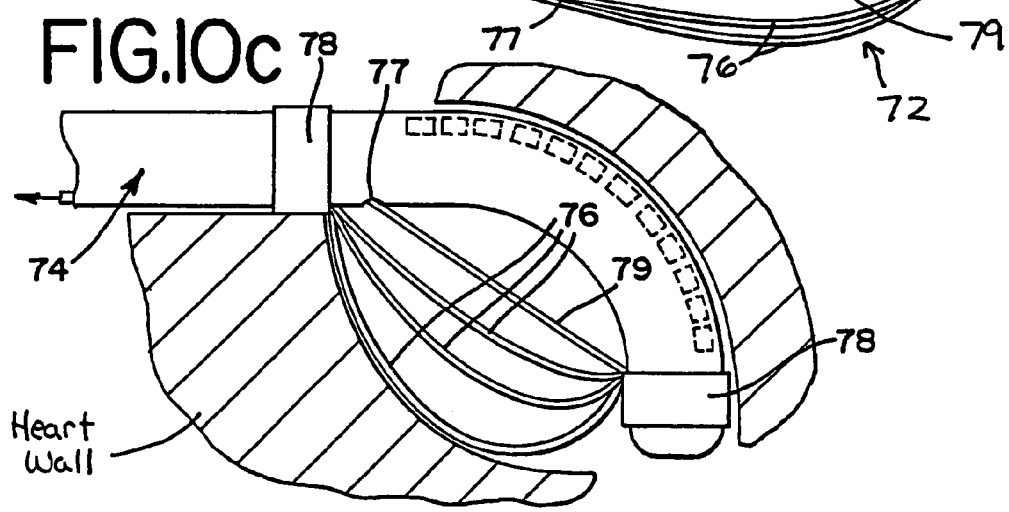

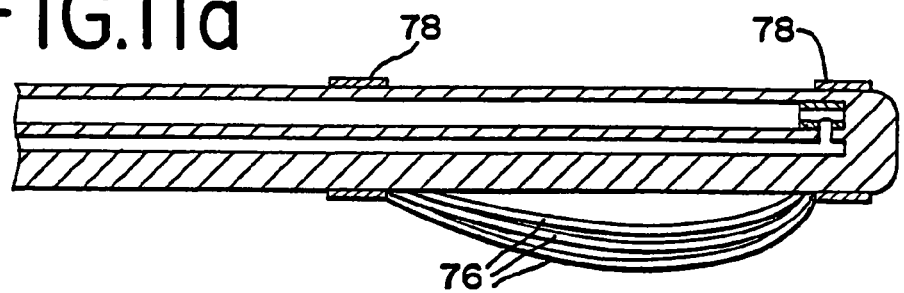
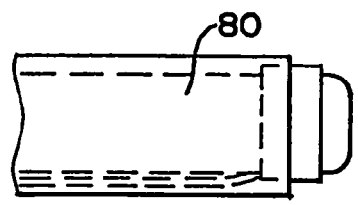
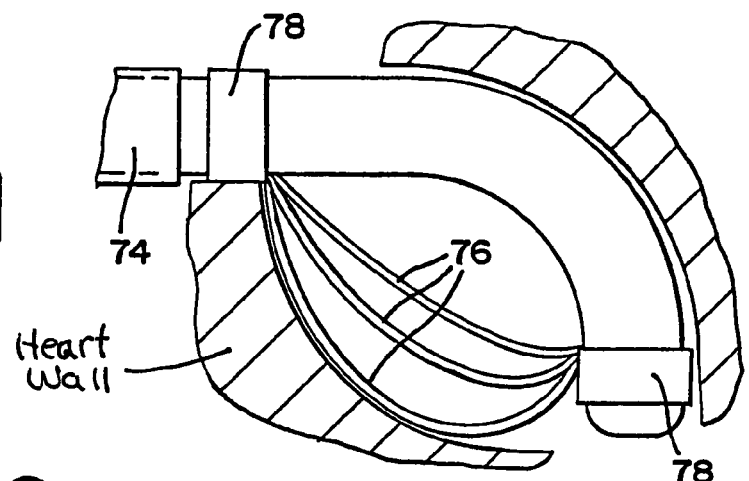
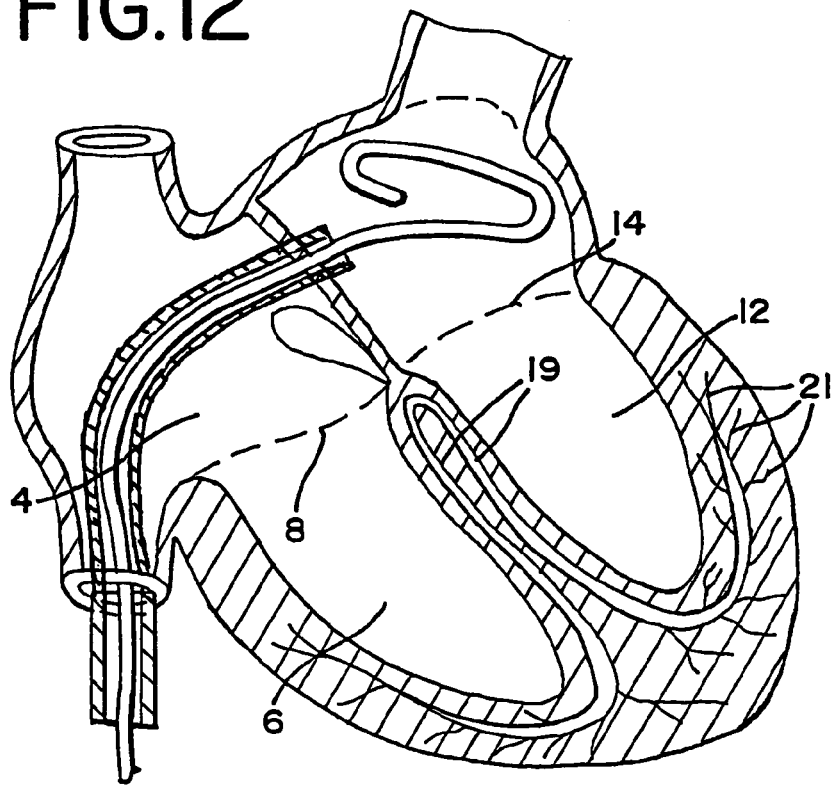

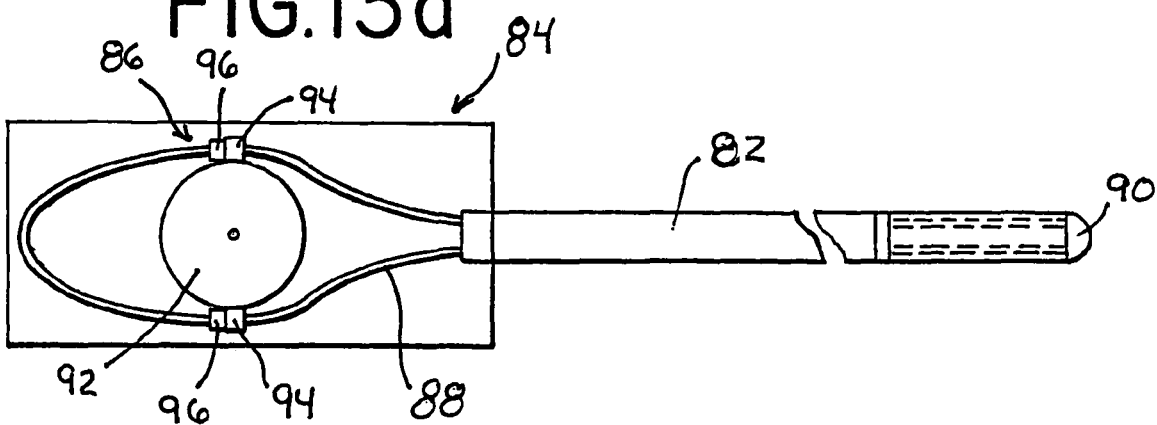
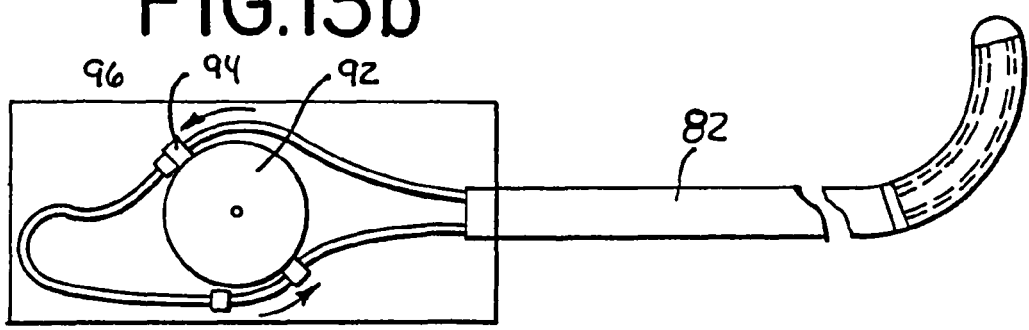
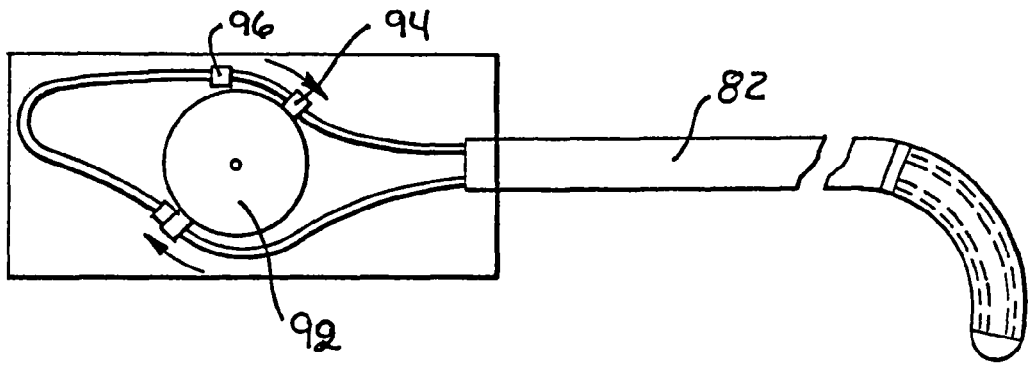

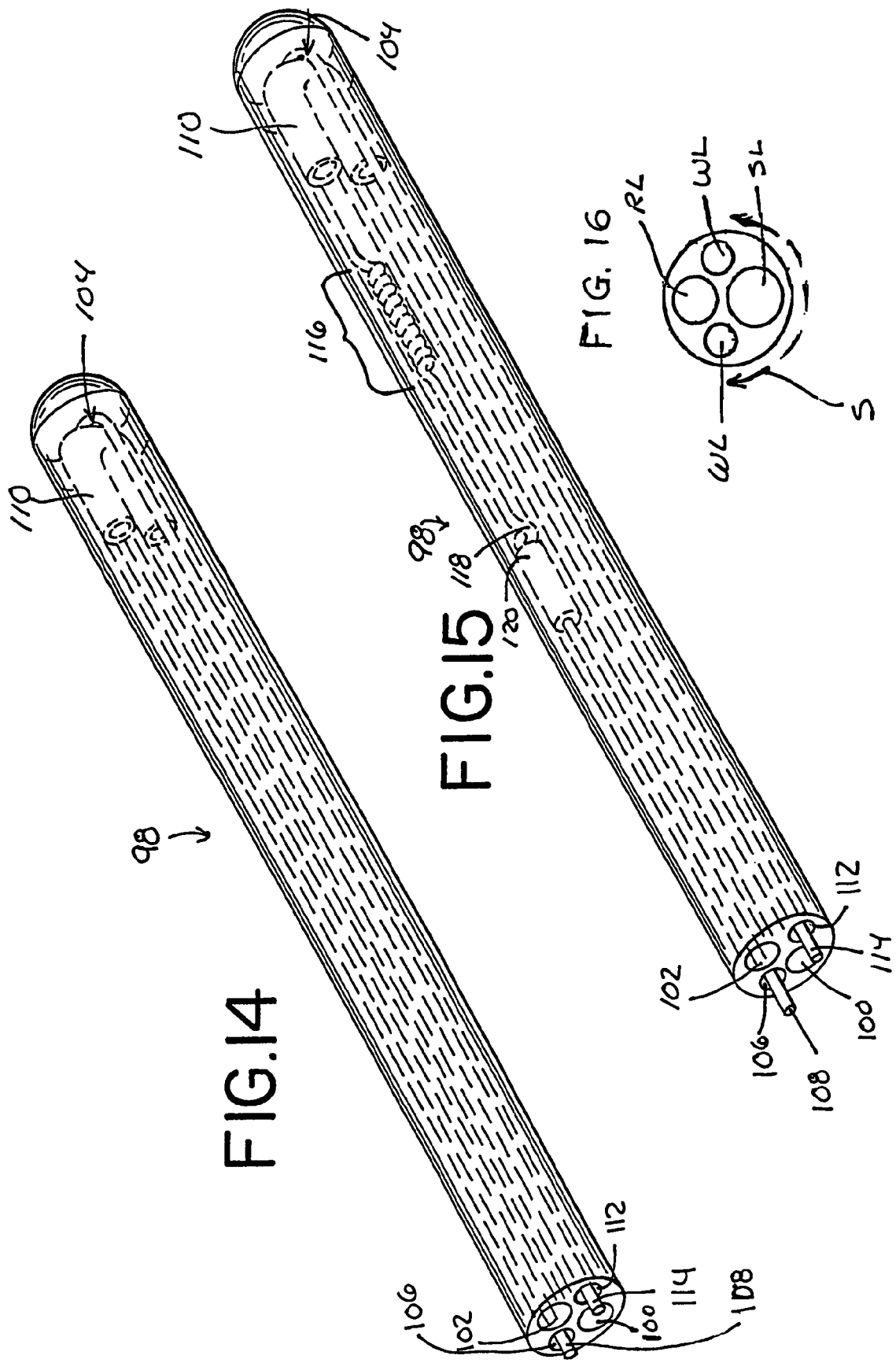

METHODS AND APPARATUS EMPLOYING IONIZING RADIATION FOR TREATMENT OF CARDIAC ARRHYTHMIA

This application claims the benefit of U.S. Provisional Patent Application Ser. No. 60/324,299, filed Sep. 24, 2001, and incorporates by reference aforesaid application.

BACKGROUND OF THE INVENTION

The present invention generally relates to the treatment of cardiac arrhythmias (atrial and ventricular) such as, but not limited to, atrial fibrillation and/or to the treatment of vascular restenosis after the use of other ablation techniques. More specifically, the present invention is directed to unique apparatus and/or methods employing ionizing radiation for ablating cardiac issue to treat cardiac arrhythmias.

The coordinated contraction of the various chambers of the human heart during a normal heartbeat is controlled by a relatively complex electrical system. The electrical signal that initiates each heartbeat begins at an area in the right atrium commonly called the "sinus node" or the "sinoatrial node." The electrical signal rapidly spreads across the right and left atria. The electrical signal is conducted to the ventricles of the heart through a connection called the atrioventricular node (AV node). From the atrioventricular node, the electrical signal passes along a bundle of special cells in the heart, known as a Bundle of His, which spreads the electrical signal rapidly through the ventricles.

The regular and normal rhythm of the heart is usually called the sinus rhythm. When the proper sequence or path of electrical signals is delayed or interrupted, an arrhythmia may develop. Anatomically, arrhythmias may be grouped according to the location where the disturbance in the electrical system arises, such as "ventricular" arrhythmias that arise in ventricles, and "atrial" or "supraventricular" arrhythmias that arise in heart tissue located above the ventricles.

In addition, arrhythmias are identified based on whether the electrical system malfunction is in the conduction of the electrical signal or impulse, or in the generation of the electrical signal or impulse. An impulse conduction failure will sometimes involve a phenomenon known as "re-entry," which occurs when the electrical signal travels in closed pathway or loop. This can occur, for example, when the AV node fails to conduct the signal properly from the atria to the ventricles, and the resultant AV nodal re-entry can cause very rapid beating of atria, sometimes called "supraventricular tachycardia." "Tachycardia" simply refers to a faster than normal heart rhythm.

One well known type of cardiac arrhythmia is known as atrial fibrillation. Atrial fibrillation, or AF, occurs when rapidly circulating abnormal electrical impulses stimulate the atrium to beat very fast—up to several hundred beats per minute or more. The rapid electrical pulses may also be passed by the AV node to the ventricles, causing fast and irregular ventricular contractions.

An increasingly well accepted procedure for treating cardiac arrhythmias in general, and atrial fibrillation in particular, is referred to as ablation. After the source of the disruption in the electrical system is determined, the tissue of the heart is ablated to eliminate the source of the aberrant impulses or to form a lesion or scar which interrupts and isolates the source of the aberrant electrical signal. It has been proposed to carry out such ablation by cryogenic probes or electrical radiofrequency (rf) energy electrodes. U.S. Pat. No. 6,161,543, for example, discloses various shapes of cryogenic probes that may be used to carry out the so-called MAZE procedure in which a series of lesions are formed strategically around the pulmonary trunk and elsewhere in the heart muscle to create an electrical maze that delays the aberrant electrical signals and prevents fibrillation of the atrium. U.S. Pat. No. 6,161,543 is incorporated by reference into this application, in its entirety.

Although cryosurgical probes and rf energy electrodes are used with increasing frequency in treating cardiac arrhythmias via heart tissue ablation, there continues to be a desire for additional apparatus and methods in the armamentarium of cardiologist for the detection and treatment of cardiac arrhythmia. For example, forming continuous linear lesions without breaks or disruptions and of uniform depth along the entire lesion lengths are challenging at the very least for cardiologists and electrophysiologists. Additionally, determination of the site of electrical malfunction requires what is known as electrophysiology mapping—which is commonly carried out as a separate procedure. It would be advantageous if the mapping and ablation could be carried out with the same instrument in the same procedure.

There also continues to be a desire for additional apparatus and methods in the armamentarium of cardiologist for the treatment or prevention of conditions resulting from the treatment of cardiac arrhythmias. For example, it is known that ablation around the pulmonary vein will sometimes result in stenosis, or closure, of the vein. Despite efforts to open the pulmonary vein and to place a stent in the vein to hold it open, patients suffering from repeated restenosis of the pulmonary vein often have a doubtful prognosis. Accordingly, there is a need to provide method and apparatus for alleviating stenosis of the pulmonary and other veins, that may be caused by other ablation treatment of cardiac arrhythmias.

SUMMARY OF THE INVENTION

The present invention is directed, in one aspect, to methods and apparatus which employ ionizing radiation for ablating heart tissue to treat cardiac arrhythmias, including without limitation both impulse conduction and impulse generation arrhythmias, and both ventricular and atrial arrhythmias. In accordance with this aspect of the present invention, an ionizing radiation source, such as a beta, gamma, x-ray or other source, is brought into immediate proximity or contact with the heart tissues to be ablated. The radiation source is of a selected activity and the contact time with the tissue (which may vary with the target tissue and can be determined without undue experimentation) is sufficient to ablate the tissue and obtain the desired treatment of the arrhythmia.

This method may be achieved by a radioactive tipped catheter or wire or, more preferably, by employing a catheter such as the Beta-Cath™ catheter (presently sold by Novoste Corporation of Norcross, Ga.) in which a train of radioactive sources are hydraulically advanced into the distal end of the catheter after it is properly positioned against the wall of the heart where the ablation is desired. The radioactive train may be of any desired length, which may be varied, to create the desired linear lesions in the heart muscle. Such a catheter lends itself particularly well to endocardial placement through the vascular system of the patient, and to the MAZE type procedure in particular. However, the present invention is not limited to an endocardial approach and includes the possible placement of the radioactive source(s) epicardially, on the outside surface of the heart, either by an open chest procedure or by a minimally invasive procedure through a trocar, endoscope or the like.

In accordance with a more specific aspect of the present invention, and particularly for endocardial applications, the delivery catheter may have means on the distal end to allow for steering and/or for active fixation of the distal end against the inner surface of the heart wall at the desired location. The fixation means may comprise, for example, a basket or nest arrangement or a loop located on the distal end of the catheter that may be deployed from a retracted position during catheter placement to a deployed position in which the basket or nest or loop rests against an opposing surface of the heart chamber to hold the catheter at the desired location for the ablation. In other words, upon deployment, the basket or nest or loop would engage against an opposing wall surface and hold or push the catheter against the inside surface of the wall or in close proximity to it at the location to be ablated. The basket or nest or loop could be deployed, for example, by releasing a pull wire attached to a pretensioned basket or nest or loop. Alternatively, the basket or nest or loop could be located in the retracted position within a sleeve or sheath that, upon axial movement, allows deployment of the basket or nest or loop.

Alternatively, the distal end of the catheter may be preformed into a desired shape, such as a classic pigtail shape or a spiral shape or loop or lasso. For example, a predetermined shape may be formed on the end of the catheter by thermally presetting or by other known techniques. Alternatively, or additionally, a guide wire could be used to assist in retaining the distal end of the catheter in the desired shape or to form an otherwise straight and flexible catheter into the desired shape.

Any of the above embodiments of the preferred catheter has the advantage of allowing the catheter to be accurately placed within the heart, and inside the atrium and the pulmonary veins in particular, before the radioactive sources are introduced into the catheter thus minimizing unnecessary radiation exposure; to create linear lines of ablation at the desired locations of selected and variable length; to permit repositioning of the catheter while the radioactive sources are outside the patient's body when treating multiple sites; and to reduce the treatment time as compared to other procedures and avoid the need to perform the highly invasive open chest MAZE surgical procedure.

In accordance with a further aspect of the present invention, ionizing radiation may be employed to modify, without complete ablation, the conduction characteristics of the AV node to treat or prevent arrhythmias arising from AV node malfunction. Prior procedures have typically required complete ablation of the AV node to treat certain arrhythmias. One drawback with this approach is that it requires permanent implantation of a pacemaker to replace the function of the AV node. Apparatus and methods which permit modification of the conduction characteristics of the AV node without complete ablation would be a particular advance over prior methods and apparatus for treating arrhythmias related to AV node malfunction, such as re-entrant tachycardias.

In connection with a further aspect of the present invention a catheter embodying the features of the present invention may be used in combination with an instrument for assessing the electrophysiology of the heart. For example the present invention may be combined with a device, such as disclosed in U.S. Pat. No. 5,529,067, which employs the Peltier effect for cooling or warming heart tissue to determine the location of aberrant electrical signals or otherwise mapping the electrophysiology of the heart.

DETAILED DESCRIPTION OF THE DRAWINGS

Additional aspects and features of the present invention may be found in the following description of the attached drawings, of which:

FIG. 3 is a diagrammatical view of a radioactive source delivery system that may be employed in the present invention.

FIG. 4 is a generally diagrammatical plan view showing conceptually a transfer device for a radioactive source for attachment to the proximal end of a radioactive source delivery catheter.

FIG. 5a is a cross-sectional view of the distal end of a radioactive source delivery catheter that may be employed in the present invention.

FIG. 5b is a cross-sectional view of the catheter of FIG. 5a, taken along line 5b-5b.

FIG. 9a is a cross-sectional view of the distal end of another embodiment of a catheter embodying the present invention, employing steering wires that may be used to adjust the shape of the distal end of the catheter.

FIG. 9b illustrates the distal end of the catheter of FIG. 9a formed into a curvilinear shape to lie against the atrial wall.

FIG. 10a is an elevational view of the distal end of another catheter embodiment that may be employed in connection with the present invention, employing a basket arrangement that is expandable from a retracted position during entry into the heart to an expanded or deployed position to urge the catheter against the heart wall at the location to be ablated.

FIG. 10b is a longitudinal cross-sectional view of the catheter of FIG. 10a taken along line 10b-10b.

FIG. 10c is an elevational view of the catheter of FIG. 10a showing the basket in an expanded or deployed position.

FIG. 11a is a cross-sectional view of the distal end of another catheter embodiment that may be used in the present invention, employing a self-expanding basket or nest to hold the catheter in the desired position for ablation.

FIG. 11b is an elevational view of the catheter of FIG. 11a with a sheath introducer overlying and compressing the basket.

FIG. 11c is an elevational view of the catheter of FIG. 11b with the sheath pulled back (or the catheter advanced) and the basket expanded to brace the catheter against the wall of the heart at the desired location for ablation.

FIG. 12 is a cross-sectional view of the human heart, showing a guide wire/catheter having a preformed distal end shape to engage the atrial wall around the ostium of one or more pulmonary veins to isolate the pulmonary vein(s) from the remainder of the atrial wall.

FIG. 13a-c showing a catheter embodying the present invention further including steering wires and a steering wire further actuating device.

FIG. 14 is a perspective cross-sectional view of a catheter embodying another inventive aspect relating to steering wire control, and illustrating a steering wire curve-accommodating segment and a steering wire bend.

FIG. 15 is a perspective cross-sectional view of catheter embodying a lumen connector in the distal end of the catheter for connecting a radiation source lumen and fluid return lumen.

FIG. 16 is a cross-sectional view of a catheter to reduce steering wire interference with radiation ablation.

MORE DETAILED DESCRIPTION

Figure 1:
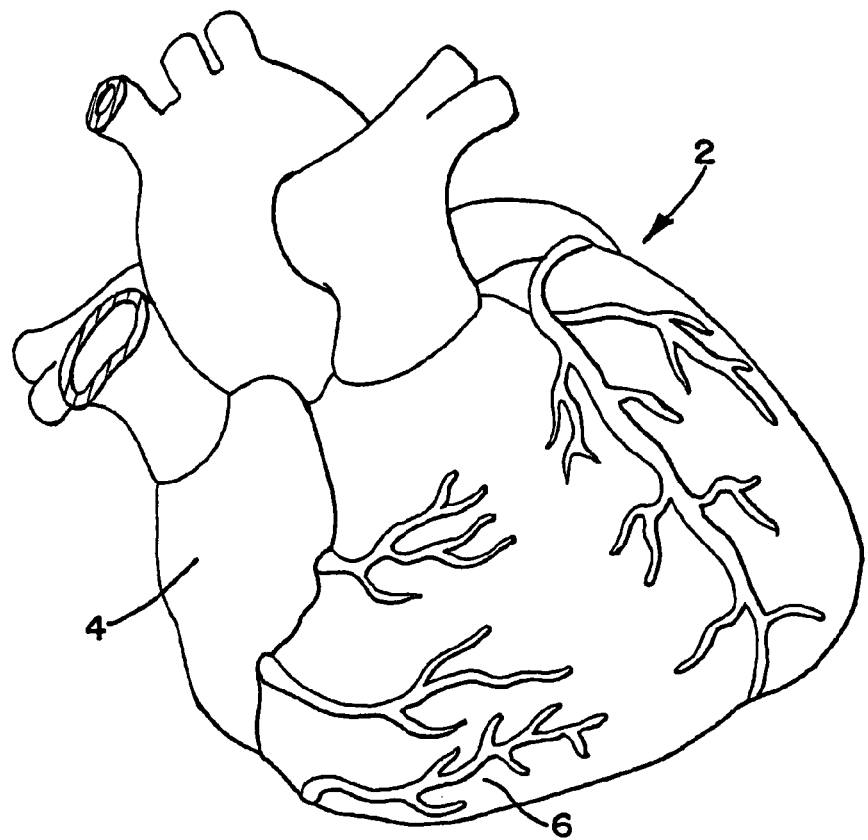
FIG. 1 is an elevational diagrammatical view of the human heart, taken from a generally anterior view.

FIG. 1 is a generally diagrammatical view of the human heart, generally designated by the numeral 2. To better understand the present invention, it is helpful to have at least a basic introduction to the physiology of the heart and to the cardiac cycle, including what is known as the electrophysiology of the heart.

The human heart has four chambers, the right atrium 4 and right ventricle 6, which are connected together by a valve 8, and the left atrium 10, and left ventricle 12 which are also connected by a valve 14. The function of the atria is to receive blood from the veins and to store it for each heartbeat. Blood returning from the major organs of the body and muscles, which is depleted of oxygen, is delivered first to the right atrium. This blood is then delivered to the right ventricle, which pumps the oxygen depleted blood to the lungs where carbon dioxide is expelled and oxygen replenished. Re-oxygenated blood flows from the lungs, through right and left pairs of pulmonary veins, to the left atrium. From the left atrium, the re-oxygenated blood flows into the left ventricle which operates as the main pumping chamber for pumping oxygen-replenished blood to the muscles and organs of the body.

As discussed briefly earlier, a normal heartbeat starts in the right atrium 4, when both of the atria 4 and 6 contract to force blood past the one-way valves 8 and 14 between the left and right atria and their respective ventricles. Quickly after contraction of the atria, the ventricles begin to contract. The one-way valves between the atria and the ventricles prevent the blood from flowing backwards. The blood expelled from each ventricle passes through another one-way valve, which closes after contraction of the ventricle.

Figure 2:
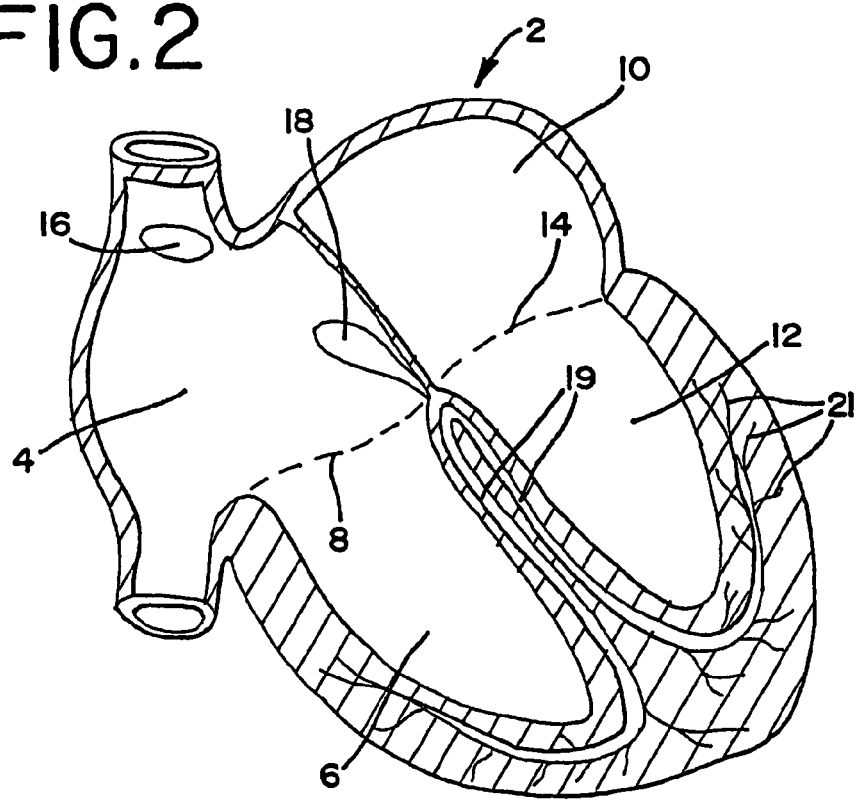
FIG. 2 is generally a cross-sectional view of the human heart of FIG. 1.

This coordinated and sequential contraction of various chambers of the heart is controlled by the heart's electrical system. Referring to FIG. 2, each normal heartbeat begins with the generation of an electrical signal or impulse from the sinus node 16 located in the right atrium 4. The impulse or signal spreads rapidly through both right and left atria, causing them to contract to force blood stored in them into their respective ventricle. The atria are electrically insulated from the ventricles except at one area, known as the atrioventricular or AV node 18. The AV node functions as the electrical distribution center for conduction of the electrical signal generated by the sinus node or any area of the atria into the ventricles. The electrical signals or impulses are conducted from the AV node through special cells that carry the impulses very quickly to the ventricular heart muscle. The special cells are arranged in bundles of fibers called the "bundle of His" 19 (or abnormal pathways recognized in the WWP syndrome for example, which are treated by "ablation" also). Eventually the fibers of the Bundle of His branch out even further into the ventricle muscle, where they are called Purkinje fibers 21.

This system of conduction rapidly transmits the electrical signal to the particular ventricular muscles, causing contraction of the ventricles to expel blood to the lungs or to the organs and muscles of the body. It should therefore be apparent how vital it is that the electrical system of the heart work properly, and that disturbances in the electrical system be promptly and effectively treated.

In accordance with present invention, delivery of the radioactive sources, apparatus and systems marketed by Novoste Corporation of Norcross, Ga. may be employed in the delivery of the radioactive sources. The Novoste™ system which is generally shown in FIG. 3 and is known as the Beta-Cath™ System, is described in detail in one or more of the following patents or published applications, each of which is incorporated by reference in its entirety into this description: U.S. Pat. Nos. 5,683,345; 5,899,882; 6,013,020; 6,261,219; 5,967,976 and 5,529,067, and PCT applications WO 00/37137 and WO 01/03761. Although the Novoste system is preferred, the broader aspects of the present invention are not limited to the Novoste system and other devices for delivering a radiation source in proximity to or contact with cardiac tissue may be used. For example, a wire or catheter with a radioactive source or ribbon located at the distal end could also be used to ablate cardiac tissue or to form lesion lines at specific locations to treat arrhythmias as described herein.

FIG. 3 depicts the Novoste™ System that may be employed in the present invention in general diagrammatic form for ease of initial understanding. Shown in FIG. 3 is an elongated catheter 20 having a proximal end portion 22, a distal end portion 24, and at least one source or send lumen 26 extending therebetween. The catheter is sized for insertion of the distal end portion through the vascular system of a patient to a selected area in the heart to be ablated, such as the AV node or other site. This may be carried out, for example, by inserting the catheter percutaneously and advancing the catheter over a typical guide wire 28 into the right atrium and/or the left atrium via transeptal puncture and catheterization. Guide wires and procedures used in advancing such a catheter to the point of ablation are well known and will not be discussed in detail.

At the proximal end of the catheter, which is located outside the patient in a percutaneous procedure such as described above, a transporting and/or loading device 30 is provided for loading a radioactive source or train of sources, such as pellets or capsules (also called "seeds") comprising or containing radioactive material, into the send lumen 26 of the catheter 20. Additional seeds may also be loaded such that the total length of the combined seeds corresponds to at least the length of the lesion to be ablated.

After the radioactive source or source train is loaded, pressurized blood-compatible liquid, such as sterile saline solution or sterile water, is introduced via liquid source 32 through a port 34 in the proximal end of the send lumen 26 behind the source(s). Flow of liquid through the lumen pushes the source (s) along the send lumen to the distal end portion, which is located at the site to be treated. The liquid which provides the motive force for moving the sources may be allowed to exit from the distal end of the catheter, but is preferably returned in a parallel return lumen provided in the catheter that communicates at the distal end of the catheter with the send lumen.

After the radioactive source or sources train is located at the desired site, it is allowed to remain for a time sufficient to ablate the tissue. It is apparent that the source train, although made up of separate radioactive seeds or pellets, provides an elongated and essentially continuous radiation source that may be used to form lines of ablated tissue through the heart, atrium, wall. The radioactive sources are preferably beta-emitting, although gamma-emitting, x-ray or other sources could be used, and the residence time period will be relatively short, on the order of minutes as discussed in more detail below. The activity of the radiation sources and the residence time may vary and be selected depending on the thickness of the heart tissue to be ablated. The precise activity and residence time is presently not fully known, but may be ascertained with routine and well know testing techniques that do not require undue experimentation.

After the treatment is complete, the catheter may be removed or shifted to a different treatment position. The radioactive sources are preferably returned to the leading device while the catheter is removed or shifted in order to avoid undue radiation exposure to the patient. To retrieve the radioactive sources, liquid may be forced through the send lumen in a reverse direction to return the treating element to the proximal end and into the loading device, if desired, before removal of the catheter. The reverse flow of fluid may be achieved by forcing liquid under positive pressure through the return lumen in a reverse direction, which forms a closed loop with the send lumen, forcing the sources in a reverse direction to the loading device 30.

FIG. 4 illustrates one form of loading device 30 in very simplified form to aid in understanding its function and structure. As seen there, the loading device, as with the preferred catheter has three separate lumen-a guide wire lumen 36 for receiving a guide wire to guide the catheter to the area of the heart to be ablated, a send lumen 38 for hydraulically forcing the source train to the distal end of the catheter and a return lumen 40, which communicates with the send lumen at the distal end of the catheter for retrieving the source train into the loading device. The guide wire lumen may extend through the entire length of the catheter or through only a distal end portion of the catheter between a distal end opening and a side opening in the catheter located proximal to the distal end opening but still in a distal portion of the catheter.

The source train is made up of a plurality of radioactive small sources or seeds 42 pre-loaded into a source train lumen 43 in radiation-shielding cartridge 44. The loading device 30 includes a receiving recess or station 46 into which the cartridge 44 may be inserted. Alignment of source train lumen 43 with the send lumen 38 allows the seeds to be ejected and transmitted along the send lumen to the distal end of the catheter. For example, a liquid-filled syringe may be attached to the send lumen 38 of the loading device to force the source train seeds to the distal end of the catheter. To remove the sources after ablation is complete, or to shift the catheter position, a syringe or other pressure source may be attached to the return lumen 40 of the device to force liquid flow in the reverse direction, returning the source train to the loading device and into the cartridge 44. A switching arrangement could be arranged in the loading device so that a single syringe could be used, and the flow switched between the send and return lumen, as required.

FIGS. 5a and 5b show the distal end of a catheter 30 that may be employed in carrying out the present invention. The catheter has a guide wire lumen 48, a send lumen 50 and a return lumen 52 connectable with the respective guide wire, send and return lumen of the loading device. The catheter is shown with a train 54 of radioactive seeds 42 located at the distal end.

The length of the source train 54 may be selected as needed to ablate a lesion of the desired length. A single radioactive element or point source may be sufficient to ablate or treat localized areas, such as modifying the properties of the AV node. However, a source train of selected length is preferred for forming linear lesions or scar tissue such as those that may be used in the MAZE procedure. Because it may be required to vary the length of the source train, the loading device may be designed to store a plurality of source trains of different lengths, so that the user can retrieve the source train of the length needed for a particular line of ablation, or to store radioactive seeds in a way that allows the user to create source trains of the different desired lengths.

Figure 6:
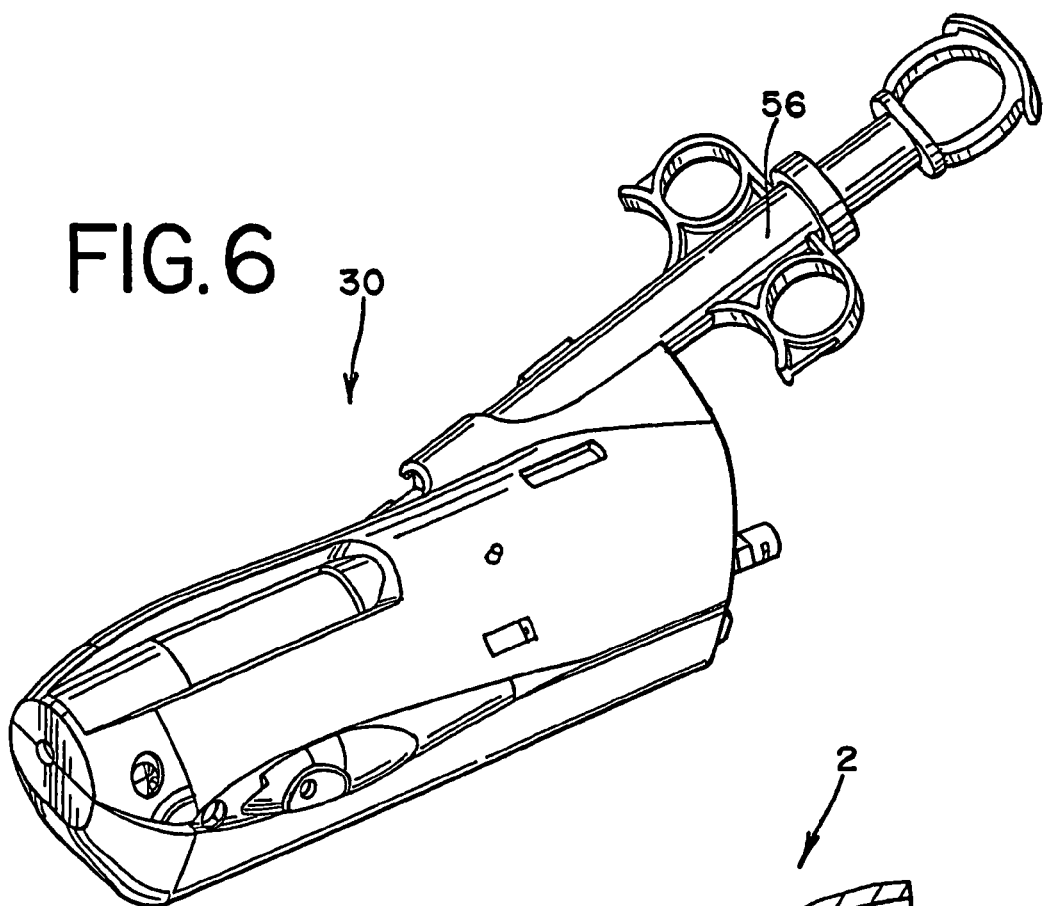
FIG. 6 is a perspective view of the radiation source delivery device and system that may be coupled to a radioactive source delivery catheter of the type shown in FIGS. 5a and 5b.

FIG. 6 illustrates a loading device 30 of more recent vintage that has a built-in syringe 56 for sending and retrieving the radioactive source train. This loading device, also called a transfer device, is described in detail in one or more of the patents and applications incorporated by reference into this application.

Figure 7A:
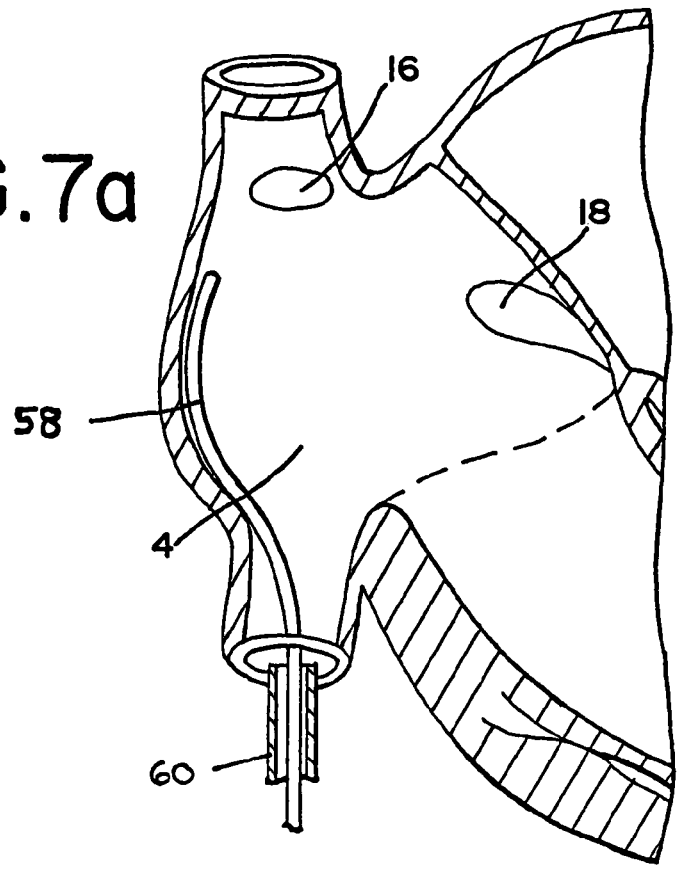
FIG. 7a is a cross-sectional view of the right atrium of the human heart, showing a guide wire having a preformed distal end shape inserted into the right atrium through an introducing catheter or sheath placed in or at the Inferior Vena Cava.
Figure 8:
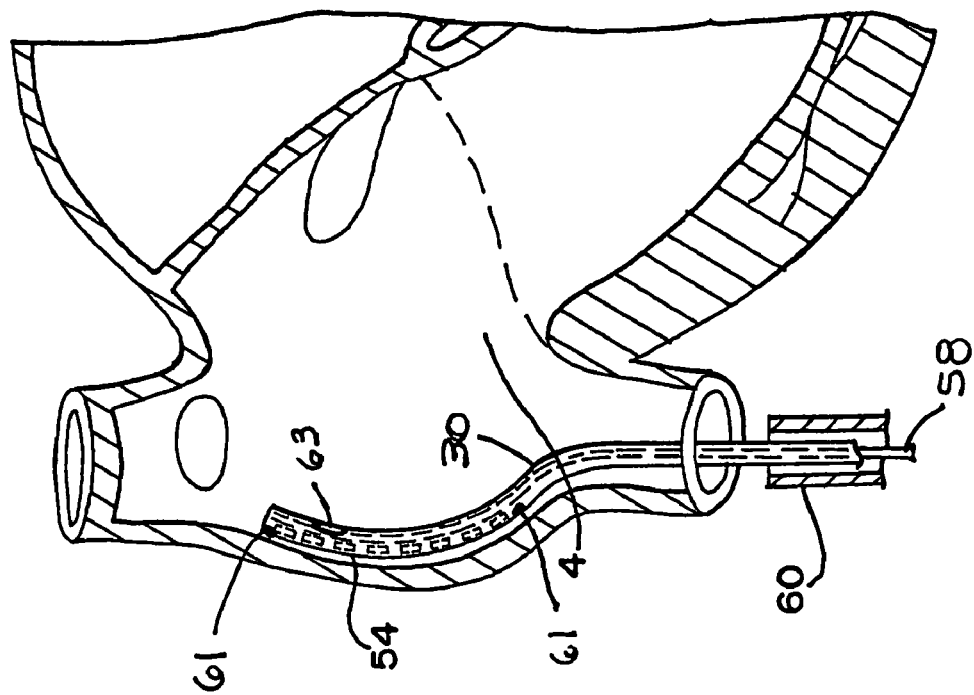
FIG. 8 depicts method and apparatus of the present invention in which a catheter is inserted into the right atrium along the pre-formed guide wire, and after a radioactive source train has been introduced into the catheter and advanced to the distal end, where they lie in close proximity to or directly against the wall of the right atrium.

FIGS. 7 and 8 illustrate the present invention employing a guide wire 58 with a preformed tip, shaped as desired, e.g. curved to conform to the wall of the heart to be ablated, to provide an active positioning means for the catheter. As shown in FIG. 7a, the guide wire is first inserted through a guide tube or sheath 60 into the right atrium 4 (preferably through the Inferior Vena Cava), where it is positioned against the atrial wall at the location to be ablated (which may be identified by a procedure called mapping).

As seen in FIG. 8, the catheter 30 in accordance with the present invention is advanced over the guide wire 58, through the guide tube or sheath 60, until it lies along the surface of the heart to be ablated. After it is inserted to the proper location, the train of radioactive seeds is advanced (as by hydraulic force) to the distal end of the catheter, which lies against the atrial wall. The radioactive seed train is allowed to remain in the distal end until sufficient radiation dose is provided to ablate a lumen lesion along the line where the distal end of the catheter lies. The radioactive seed train may then be retrieved for repositioning or removal of the catheter. Because the radiation sources are, not located in the catheter during introduction, positioning or withdrawal, overexposure of the heart to radioactivity is minimized.

Figure 7B:
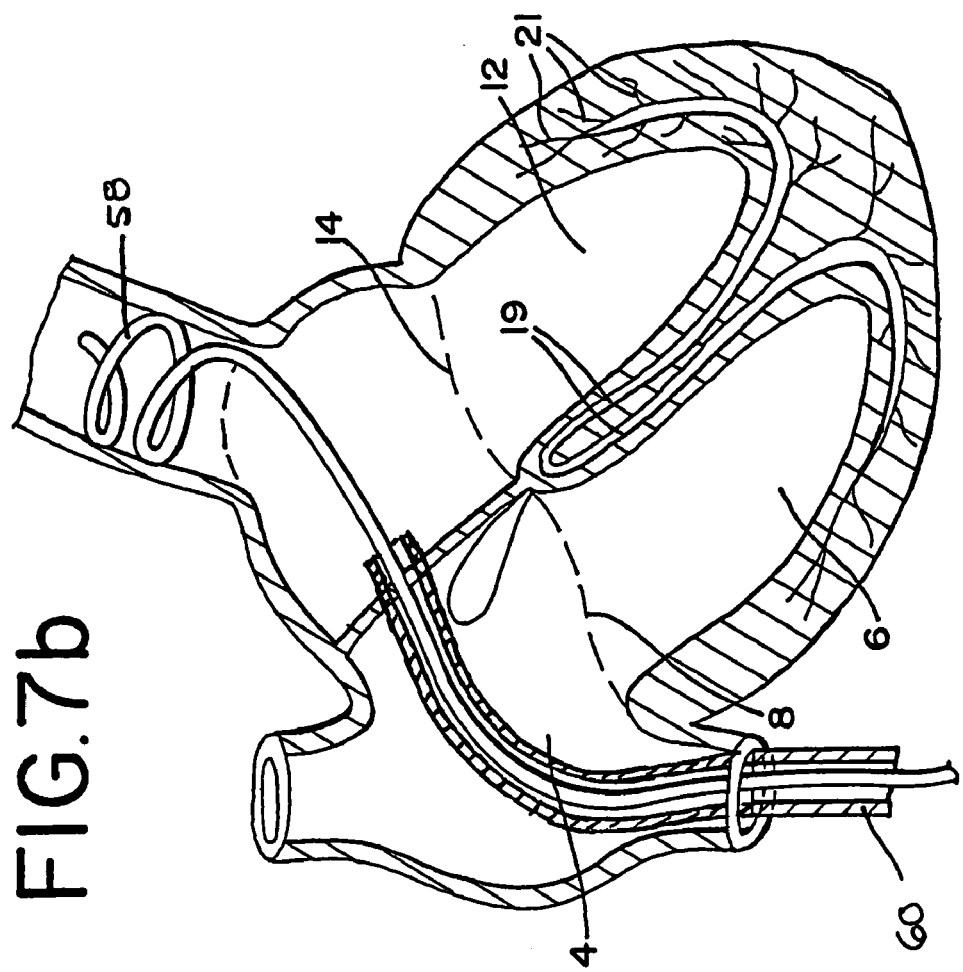
FIG. 7b is a cross-sectional view of the human heart, showing a guide wire having a preformed distal end pig-tail or spiral shape inserted into the pulmonary vein through an introducing catheter or sheath placed in or at the Inferior Vena Cava.

FIG. 7b illustrates, similar to FIG. 7a, a guide wire of alternative shape. FIG. 7b shows a loop, spiral or pig-tail shaped guide wire that may be used to form a line of ablation around the pulmonary vein. Although shown as a spiral or pigtail shape, any other suitable shape may also be used to form the line of ablation, and the present invention is not limited in its broader aspects to the particular guide wire shape. As illustrated, one means of entry into the pulmonary vein is into the right atrium (preferably using the femoral approach which accesses the right atrium through the Inferior Vena Cava), through the atrial septum and into the left atrium and pulmonary vein. Of course, other approaches to the pulmonary vein may be used without departing from the present invention. For treating atrial fibrillation, the guide wire or catheter may be shaped to form a continuous lesion or ablation in the atrial wall, isolating the pulmonary vein(s) from the remainder of the left atrium. The spiral or pigtail shape is particularly useful for locating the radiation source catheter within a pulmonary vein itself and treating pulmonary vein stenosis by exposing the interior or inside surface of the pulmonary vein to a stenosis-inhibiting dose of ionizing radiation. Alternatively, the guide wire portion located in the pulmonary vein could be straight and generally centrally located within the vein.

It is contemplated that these alternative shapes would be used with a radiation source delivery catheter having a sufficiently flexible distal end to conform to the shape of the guide wire. The guide wires of FIGS. 7a and 7b could be of any suitable material, such as stainless steel, titanium or nickel-titanium alloy.

Alternatively, the catheter itself could have a pre-shaped distal end, such as curved, pig-tail or spiral to engage the heart wall in the desired position for ablation. This shape could be set into the end of the catheter using known techniques such as heat setting, molding or the like. With this type of catheter, the guide wire would tend to straighten the catheter during insertion, and withdrawal of the guide wire would allow the catheter to resume its preset shape. After properly positioned against the wall of the heart at the location to be ablated, the radioactive sources would be inserted into the end of the catheter for the ablation treatment.

The catheter (see FIG. 8) may also have electrode(s) or sensor(s) 61, such as bipolar, carried at the distal end portion and communicating via conductors extending through the catheter to a proximal location outside the patient's body. At least one such electrode is contemplated, and preferably at least two electrodes or sensors, such as one proximal to the radiation source and one distal to the radiation source. Two electrodes or sensors would allow sensing of conductivity across a line of ablation to determine if ablation is complete. Also, the electrodes would allow for direct sensing and monitoring or electrophysiological characteristics of the heart tissue before, during and/or after ablation, and well all mapping the electrophysiology of the heart to determine the appropriate site for radiation ablation or treatment. The electrodes would be connected through one or more conductors extending through the catheter to a monitoring or readout device located outside the patient's body.

Further, the catheter may include a cooling surface 63 on the distal end portion for cooling selected cardiac tissue, for example, to identify the desired site for ablation or other radiation treatment. This cooling surface could be based on the Peltier effect, as disclosed for example. in the previously mentioned U.S. Pat. No. 5,529,067, and also connected via one or more conductors extending through the catheter. More specifically, systematic cooling of selected heart tissue and observation of the effect of cooling on the electrophysiology may be used to identify the location of tissue to be ablated or treated, and once identified, the treatment can be immediately carried out by advancing the radiation source through the catheter and to the site without further movement of the catheter required. This has the potential benefit of better assuring that treatment is being carried out at the desired location.

FIGS. 9a and 9b show an alternative positioning means for actively. and positively positioning the distal end of a radiation delivery catheter 62. The catheter 62, as shown there, includes at least a source send lumen 64 and a parallel fluid return lumen 66 extending between the proximal and distal end portions of the catheter. Opposed steering wires 68 are embedded in or otherwise attached to the tip end of the catheter, 180° apart, and extend through smaller diameter steering wire lumens 70 that extend the length of the catheter parallel to the send and return lumens for remote control outside the patient's body. By pushing or releasing one steering wire and pulling the other steering wire, the tip end of the catheter may be bent or curved in varying degrees toward the wire that is pulled for positioning against the wall of the heart, as seen on FIG. 9b, or for steering the catheter to the desired location in the heart. The catheter described above could also be employed with only a single steering wire and steering wire lumen, which would allow bending in one direction only.

It is preferable that the steering wires not be located between the radiation source and the line of tissue to be ablated, because this may result in attenuation of the radiation or a disturbance in the radiation dose distribution. In an alternative embodiment, the steering wire lumens may be positioned differently in relation to the radiation source and fluid delivery lumens, as shown in FIG. 16. The catheter shown there also has four lumens: a radioactive seed send or delivery lumen SL, a fluid return lumen RL, which may alternatively be elliptical rather than round for less pressure and faster seed delivery, and two smaller steering wire lumens WL that are between and offset from (not in alignment with) the other two delivery/return lumens. The two smaller lumens house steering wires that are attached to the distal end of the catheter and give the catheter bi-directional steering capabilities. The steering wires may be embedded within the closed distal end of the steering wire lumens or otherwise attached to the distal end of the catheter. The construction shown in FIG. 16 allows essentially an entire side S (180°) of the catheter to lie against the cardiac tissue for ablation without interference from the steering wires. All four lumens can be extruded as a single piece or can be formed separately and fused together and closed off at the tip. With two steering wires, there will of course be a conventional operating mechanism for each at the proximal end of the catheter.

FIGS. 10a-10c show another positive positioning means for the catheter employing an expandable cage or basket 72 that braces the distal end of the catheter 74 against the heart wall at the place of ablation. As seen in FIG. 10, the nest or basket preferable employs a plurality of elongated members, such as ribs or spokes 76 that extend between a pair of spaced-apart retainers 78 located on the distal end of the catheter. The retainers 78 may comprise circumferential bands of heat-shrunk plastic or other materials, preferably recessed into the surface of the catheter to provide a generally smooth surface for advancing through a guide tube or sheath. The retainers tightly hold each end of the spokes, so that the spokes must flex when the tip is bent. The retainers may also be metallic or have a metallic coating and function as electrodes in addition to the rib-retaining function.

The spokes 76 may be of thin stainless steel, plastic or other suitable material and. are pre-arranged, as by pre-stressing, to expand away from the catheter when the tip end is bent, as shown in FIG. 10c, and to return substantially to their original position extending generally parallel to the catheter, as seen in FIGS. 10a and 10b, when the tip is allowed to return to its original shape. The tip may be curved by the use of a pull wire 79 that extends from the tip of the catheter through a side aperture 77 located in the wall of the catheter at a location spaced from the tip end. By pulling on the wire, the tip is bent, and the spokes bend to the expanded position. Releasing the pull wire allows the spokes and catheter tip to return essentially to the original position. Although illustrated with the catheter on the outside of the basket, the spokes could be arranged around the distal end of the catheter so that the catheter is located within the basket. In such an arrangement, the distal end of the catheter may not be in direct contact with the heart wall, but closely adjacent or in close proximity to the heart wall.

In accordance with another alternative of the present invention, the spokes themselves could be radioactive, such as by coating with a radioactive material, having a radioactive material imbedded in them or other technique. In this arrangement, the spokes need not be parallel to one another, but may be arranged in such a pattern as desired to form multiple oblique lines of ablation within the heart upon deployment of the basket in contact with the heart wall.

FIGS. 11a-11c show an alternative basket or nest or cage arrangement for actively positioning the catheter tip. In this embodiment, the spokes 76 are preformed or preset to the position shown in FIG. 11c. A sheath or sleeve 80 overlying the spokes holds them in a retracted position, as seen in FIGS.

11a and 11b. When the sleeve is pulled axially or longitudinally in the proximal direction, the spokes are uncovered and the spokes are allowed to move to their expanded or deployed position (as seen in FIG. 11c), bracing the tip of the catheter against the heart wall.

In addition to stainless steel or plastic, the spokes in this embodiment may be a shape memory alloy or plastic composition, e.g., nickel-titanium alloy sometimes called ("nitinol"), which has different properties at different temperatures. For example, the spokes may be assembled and the sleeve placed over them at very low temperatures, where they are very plastic and easy to assemble. After warming to room temperature or higher, the metal has a tendency to assume an expanded or other state that is particularly well suited for forming a basket or cage arrangement to hold the catheter tip against the heart wall or in close proximity to it. To remove or reposition the catheter, the sleeve would be advanced over the spokes to hold them in the retracted position.

The fixation device is not necessarily an expandable cage, but other fixation devices such as an expandable balloon, vacuum port(s) in the catheter wall or anchors may be used to affix the catheter at the desired location. A balloon attached to one side of the catheter (extending less than 360°, and preferably less than 180° around the catheter shaft) may be used for example to brace the catheter against the heart tissue to be ablated. Such a catheter would appear similar to that shown in FIG. 11, but with a balloon in place of the spokes and with the addition of an inflation lumen extending between the proximal and distal end portions of the catheter and in fluid communication with the balloon. Alternatively, one or more vacuum ports may be provided in the catheter wall in a manner like that shown in U.S. Pat. No. 6,139,522, incorporated by reference. Barbs, hooks and spiral screws or the like may also be used on the distal end portion of the catheter, as shown in the above patent, to affix the catheter in proximity to or contact with the cardiac tissue to be ablated or otherwise treated by ionizing radiation from the source.

In addition to the features and functions described above, other aspects of the invention include having the distal end of the catheter more flexible than the main body of the catheter for improved steerability and/or less tissue trauma. Also, catheters may be used with or without guide wires. The preshaped guide. wires or pre-shaped catheters may have other shapes in addition to pig-tail or spiral.

It is known that ablation around the pulmonary vein using prior rf ablation techniques may result in stenosis, which is a closure, of the pulmonary vein. Stents have been used, sometimes unsuccessfully, to hold the vein open after an angioplasty procedure is performed to reopen the vein. It has been suggested by others that the Novoste™ Beta-Cath™ System may be used to treat or avoid restenosis of the pulmonary vein after such ablation by irradiating the inside of the pulmonary vein with ionizing radiation.

One or more of the apparatus described above could be used to-treat restenosis of the pulmonary vein by applying an appropriate dose of radiation to the site of the ablation. For example, the basket or cage fixing means may be used to position the radiation delivery catheter at the desired location within the pulmonary vein, with the catheter in close proximity to the area of ablation, to diminish the growth of scar tissue (a predominant factor in stenosis following damage to blood vessels by angioplasty, stents and the like). Or a pigtail or spiral shaped guide wire could be used with a radioactive source delivery catheter for achieving the same objective.

FIG. 12 illustrates employment of a catheter of the present invention to form a line of ablation or a lesion in the atrial wall around the ostium of a pulmonary vein. The catheter may have a preformed tip that, upon withdrawal of the guide wire, forms a circle or loop of a size sufficiently large to encircle the ostium of the pulmonary vein. After placing against the atrial wall around the ostium, a radiation source of sufficient length to encircle the ostium would be advanced to the distal end of the catheter to form the lesion encircling the pulmonary vein. Alternatively a shorter radiation source could be used, and the position of the radiation source periodically changed until a complete lesion is formed around the ostium.

Although shown ablating a line around a pulmonary vein, the above method could be used to form a lesion line around more than one pulmonary vein simultaneously.

FIGS. 13a-c illustrate a catheter 82 of the present invention with steering wires for changing the shape of the distal end portion, and a proximal handle portion 84 with an actuator 86 for adjusting the shape of the distal end. As shown there, a preferably continuous wire 88 is employed. The catheter includes two steering wire lumens (although a single lumen may be used for both wires) that extend between the handle, which is attached to the proximal end of the catheter, and the distal end of the catheter. One end of the wire extends through one such lumen and terminates at the distal end of the catheter, where it is attached to the tip 90. The other end of the wire extends through the other lumen and also terminates at the distal end of the catheter, where it is attached to the tip. The steering wire receiving lumen are about 180° apart so that pulling on one wire while releasing or pushing on the other causes the tip to deflect in the direction of the pulled wire. Thus, the catheter tip may be deflected in two different and opposed directions as shown in FIGS. 13b and 13c.

For purposes of illustration, and not limitation, the steering wire controller is generally illustrated as a rotating pulley or wheel 92 with opposed steering wire guides 94 through which the steering wire is slidably received. The steering wire has stop members 96 located for engagement by the guides when the wheel 92 is turned. With this arrangement, turning the wheel results in pulling one wire and releasing the other to bend the tip toward the pulled wire. Reversing the direction of the wheel reverses the direction of tip curvature.

Although this embodiment employs a single length of wire or cable to form both of the steering wires, it should be apparent that separate wires could be used without departing from the broader aspects of this invention. This steering wire construction also is not limited to a radiation source catheter, but may be used in any catheter that needs to navigate tortuous body passageways, such as cardiology catheters.

FIGS. 14 and 15 show additional features of a modified steering wire and a distal tip lumen connector. FIG. 15 shows a steering wire construction that is not limited to a radiation delivery catheter or to use in cardiac ablation, and may be employed in other catheters, particularly cardiology catheters, where navigating a tortuous body lumen is necessary.

The catheter 98 shown in FIG. 15 for illustrative purposes only is a radiation source delivery catheter, such as described generally above. The catheter is elongated and flexible, and has a proximal end portion and a distal end portion. The catheter includes a radiation source lumen 100 and a fluid return lumen 102. A single wire, generally at 104, extends through steering wire lumen 106 to form steering wire 108, curves at the distal end of the catheter around a lumen connector 110 and returns through steering wire lumen 112 to form steering wire 114. The distal end of the steering wire 104, which curves around the lumen connector, may be fixed to the distal tip end of the catheter by adhesive, bonding, interference fit, or suitable means or may otherwise be in a fixed non-moving relationship to the lumen connector so as to transmit forces applied by the steering wires to the distal tip.

Of course, the steering wire is not necessarily continuous and the individual steering wires 108 and 114 could be separate and individually attached in the distal tip of the catheter while still benefiting from the aspects of the present invention shown in FIG. 15. Similarly, although the steering wire lumens are shown about 180° apart, that could also be varied as desired to vary the shape of the bend imparted to the distal end of the catheter.

As seen there, one steering wire includes a bend or curve-accommodating segment, generally at 116. Such a segment could be located in both wires, if so desired. The bend-accommodating segment 116 is formed of a plurality of undulations in the steering wire and is preferably in the form of a plurality of coils like a coil spring. This segment allows for greater curvature when tension is placed on the other steering wire. The curve-accommodating segment gives elongation to the wire for a tighter (smaller) radius of curvature. It is understood that when the steering wire 114 is pulled or tension applied, the curve accommodating segment is, in effect, pushing the other steering wire—the combination of tension and compression results in smaller radius of curvature.

The illustrated catheter 98 in FIG. 15 includes another steering wire feature that allows the distal end portion of the catheter to be curved in predetermined direction. Steering wire 108 includes a bend 118 that engages against an obstruction 120 located in lumen 106 when the wire is pulled, causing the wire to curve at the bend. In the illustrated embodiment, the bend 118 is generally V-shaped and located proximally of the bend-accommodating segment, and the obstruction is defined by a plug fused or bonded in the lumen 106, and the steering wire 108 slidably extends through the plug. When the steering wire is pulled, the bend 118 engages against the end of the plug, forcing the wire to bend in a direction opposed to the bend 118. With this feature, the catheter may be caused to bend at a particular location, i.e., at the bend 118, and all or some of the portion of the catheter distal to bend 118 can remain essentially straight.

The bend feature could, of course, be used in a steering wire that does not have a bend-accommodating segment 116. However, by having both features in the same steering wire it is possible to cause the distal portion of the catheter to bend in two different directions simultaneously with a relatively small radius of curvatures in at least one of those. For example, by pulling on both steering wires, the engagement between the bend 118 and the plug 120 causes the distal end to bend in a direction opposite the bend. Pulling of steering wire 114 causes the more distal tip portion to bend in the direction that steering wire 114 is being pulled, and the bend accommodating segment 116 allows that bend to be of an even smaller radius than could otherwise be achieved. This could result, for example, in the distal end portion extending in a plurality of different directions For example, the distal end portion could have a generally L-shaped bend at bend 118 and a generally C-shaped curve at curve-accommodating segment 116, or it could have a generally S-shape. The curves could be in the same plane or in different planes, affording a variety of shapes to the surgeon for navigating through complex body lumens, or for positioning the catheter against or in proximity to the tissue to be treated.

The illustrated tubular U-shaped lumen connector 110 located in the distal tip of the catheter connects the source and return lumens in fluid communication. The lumen connector allows the fluid, which transports the radioactive source to the distal end portion, to return to the proximal end portion. It is preferably metallic or of rigid plastic construction and also serves to add strength and stability to the end of the catheter.

Additional features and advantages may be apparent to one skilled in the filed upon review of this description, and it is intended that the application include such obvious variations and changes that may be made without departing from the present invention.

The invention claimed is:

1. A method for ablating cardiac tissue comprising exposing the cardiac tissue to ionizing radiation from an ionizing radiation source in proximity to or contact with the cardiac tissue.

2. The method of claim 1 in which the ionizing radiation source is elongated and essentially continuous, and a line of ablated cardiac tissue is formed.

3. The method of claim 2 in which the elongated radiation source comprises a plurality of individual radiation sources disposed in a line to define the elongated source.

4. The method of claim 3 in which the elongated radiation source is advanced along the catheter by fluid pressure.

5. The method of claim 1 in which the radiation source is brought into proximity to or contact with an endocardial surface.

6. The method of claim 1 in which the radiation source is brought into proximity or contact with an epicardial surface.

7. The method of claim 1 in which the radioactive source is held by a fixation device in immediate proximity to or contact with the cardiac tissue to be ablated.

8. The method of claim 1 comprising positioning a distal end portion of an elongated catheter in immediate proximity or contact with cardiac tissue to be ablated and advancing the ionizing radiation source through the catheter to a location adjacent to the cardiac tissue to be ablated.

9. The method of claim 8 in which the catheter includes a cooling surface disposed on the distal end portion and the method includes selectively contacting cardiac tissue with the cooling surface to identify the tissue to be ablated.

10. The method of claim 8 in which the catheter includes an electrode on the distal end portion to sense an electrophysiological characteristic of the cardiac tissue.

11. The method of claim 8 in which the catheter is inserted through the atrial septum.

12. The method of claim 8 in which the distal end portion of the catheter is sufficiently flexible to conform to the shape of a guide wire, and the method includes advancing the distal end portion of the catheter along a guide wire to the cardiac tissue to be ablated.

13. The method of claim 12 in which the distal end portion of the catheter includes a pre-formed shape that it assumes upon withdrawal of the guide wire from the distal end portion.

14. The method of claim 13 in which the pre-formed shape is a spiral.

15. The method of claim 8 further comprising steering the distal end potion of the catheter to cardiac tissue to be ablated.

16. The method of claim 15 wherein the steering comprises adjusting the shape of the distal end portion.

17. The method of claim 8 in which the distal end portion of the catheter is held by a fixation device in proximity to or contact with the cardiac tissue to be ablated.

18. The method of claim 1 in which said method includes forming a line of ablated tissue isolating one or more pulmonary veins from the remaining portion of the left atrium.

19. The method of claim 1 in which the ionizing radiation source is a beta radiation source.

20. The method of claim 1 including selectively cooling the cardiac tissue to identify the tissue to be ablated.

21. The method of claim 1 further comprising sensing an electrophysiological characteristic of the cardiac tissue.

22. A method for modifying the conduction characteristics of the AV node of a human heart comprising exposing the cardiac tissue comprising the AV node to ionizing radiation from an ionizing radiation source in immediate proximity to or contact with such tissue without completely ablating the AV node.

23. The method of claim 22 comprising positioning a catheter in immediate proximity to or contact with the cardiac tissue comprising the AV node and advancing the ionizing radiation source through the catheter to a location adjacent to such tissue.

24. The method of claim 23 in which the catheter includes a cooling surface disposed on the distal end portion and the method includes selectively contacting cardiac tissue with the cooling surface to identify the tissue to be treated.

25. The method of claim 22 wherein the conduction characteristic of the AV node is modified to treat re-entrant tachycardia.

26. The method of claim 22 in which the radioactive source is held by a fixation device in immediate proximity to or contact with the cardiac tissue comprising the AV node.

27. The method of claim 22 including selectively cooling the cardiac tissue to identify the tissue to be treated.

28. The method of claim 22 in which the ionizing radiation source is a beta radiation source.

29. A method for treating atrial fibrillation comprising:
defining a plurality of lines of ablated tissue in the wall of the left atrium by exposing selected cardiac tissue to ionizing radiation from an ionizing radiation source in proximity to or contact with the selected tissue.

30. The method of claim 29 in which the ionizing radiation source is elongated and essentially continuous.

31. The method of claim 30 in which the elongated radiation source comprises a plurality of individual radiation sources disposed in a line to define the elongated source.

32. The method of claim 29 in which the radiation source is brought into immediate proximity or contact with an endocardial surface.

33. The method of claim 32 in which the radioactive source is held by a fixation device in immediate proximity to or contact with the cardiac tissue to be ablated.

34. The method of claim 29 in which the radiation source is brought into immediate proximity or contact with an epicardial surface.

35. The method of claim 29 comprising positioning a distal end portion of an elongated catheter in immediate proximity or contact with cardiac tissue to be ablated and advancing the ionizing radiation source through the catheter to a location adjacent to the cardiac tissue to be ablated.

36. The method of claim 35 in which the elongated radiation source is advanced along the catheter by fluid pressure.

37. The method of claim 29 in which the ionizing radiation source is a beta radiation source.

38. A method for treating pulmonary vein stenosis comprising exposing the interior surface of the pulmonary vein to ionizing radiation from an ionizing radiation source in proximity to or contact with such surface, wherein the ionizing radiation source is advanced along an elongated catheter by fluid pressure.

39. The method of claim 38 in which the ionizing radiation source is elongated and essentially continuous.

40. The method of claim 39 in which the radiation source comprises a plurality of individual radiation sources disposed in a line to define the elongated source.

41. The method of claim 38 comprising positioning a distal end portion of the elongated catheter in immediate proximity or contact with the interior surface of the pulmonary vein and advancing the ionizing radiation source through the catheter to a location adjacent to the tissue to be treated.

42. The method of claim 41 in which the catheter is inserted through the atrial septum.

43. The method of claim 41 in which the distal end portion of the catheter is sufficiently flexible to conform to the shape of a guide wire, and the method includes advancing the distal end portion of the catheter along a guide wire to the inside of the pulmonary vein.

44. The method of claim 43 in which the distal end portion of the catheter includes a pre-formed shape that it assumes upon withdrawal of the guide wire from the distal end portion.

45. The method of claim 44 in which the pre-formed shape is a spiral.

46. The method of claim 38 in which the ionizing radiation source is a beta radiation source.

47. A method for treating pulmonary vein stenosis comprising exposing the interior surface of the pulmonary vein to ionizing radiation from an ionizing radiation source in proximity to or contact with such surface; and wherein a distal end portion of the catheter is sufficiently flexible to conform to the shape of a guide wire, and the method includes advancing the distal end portion of the catheter along a guide wire to the inside of the pulmonary vein.

* * * * *